United States Patent
Kumar et al.

(10) Patent No.: US 7,129,365 B2
(45) Date of Patent: Oct. 31, 2006

(54) PROCESS FOR THE PREPARATION OF ACITRETIN

(75) Inventors: Yatendra Kumar, Haryana (IN); Mohan Prasad, Haryana (IN); Kaptan Singh, Pradesh (IN); Pankaj Sharma, New Delhi (IN)

(73) Assignee: Ranbaxy Laboratories Limited, Haryana (IN)

( * ) Notice: Subject to any disclaimer, the term of this patent is extended or adjusted under 35 U.S.C. 154(b) by 0 days.

(21) Appl. No.: 10/484,394

(22) PCT Filed: Jul. 11, 2002

(86) PCT No.: PCT/IB02/02727

§ 371 (c)(1),
(2), (4) Date: May 18, 2004

(87) PCT Pub. No.: WO03/007871

PCT Pub. Date: Jan. 30, 2003

(65) Prior Publication Data

US 2004/0192949 A1 Sep. 30, 2004

(30) Foreign Application Priority Data

Jul. 19, 2001 (IN) .............................. 777/Del/01

(51) Int. Cl.
*C11B 3/00* (2006.01)
(52) U.S. Cl. ..................... 554/206; 554/207; 554/212
(58) Field of Classification Search ................ 554/206, 554/207, 212
See application file for complete search history.

(56) References Cited

U.S. PATENT DOCUMENTS

| 2,935,449 A | 5/1960 | Bavley et al. ................. 167/81 |
| 3,268,606 A * | 8/1966 | Jaeger ......................... 435/67 |
| 4,105,681 A | 8/1978 | Bollag et al. ............... 260/404 |

FOREIGN PATENT DOCUMENTS

| RU | 2001903 | 10/1993 |
| WO | WO 98/03480 | 1/1998 |
| WO | WO98/03480 | * 1/1998 |

OTHER PUBLICATIONS von Milan Soukup et al., "46. New Approaches to Some Aromatic Retinoids", *Helvetica Chimica Acta*, 72:370-376 (1989).
Makuh et al., *Zh. Org. Chem.*, 25(4):792-797 (1989) (See Notes).
Andriamialisoa et al., "A new stereoselective synthesis of Acitretin.", *Helvetica Chimica Acta.*, 85:2926-2929 (2002).
Aurell et al., "Trienediolates of Hexadienoic Acids in Synthesis. Addition to Unsaturated Ketones. A Convergent Approach to the Synthesis of Retinoic Acids.", *Tetrahedron*, 51(13):3915-3928 (1995).

* cited by examiner

*Primary Examiner*—Deborah D. Carr
(74) *Attorney, Agent, or Firm*—Jayadeep R. Deshmukh, Esq.; George E. Heibel, Esq.; William D. Hare, Esq.

(57) ABSTRACT

The present invention relates to a cost effective and industrially useful process for the preparation of substantially pure acitretin. More specifically, the present invention relates to the preparation of acitretin of high purity and yield.

6 Claims, No Drawings

PROCESS FOR THE PREPARATION OF ACITRETIN

FIELD OF THE INVENTION

The present invention relates to a cost effective and industrially useful process for the preparation of substantially pure acitretin. More specifically, the present invention relates to the preparation of acitretin of high purity and yield.

BACKGROUND OF THE INVENTION

Acitretin, an aromatic analogue of retinoic acid, is useful in the treatment of hyperkeratotic skin diseases such as psoriasis. It is a member of the retinoid family, a group of compounds related to retinol (vitamin A). Chemically, acitretin is (all-E)-9-(4-methoxy-2,3,6-trimethylphenyl)-3,7-dimethylnona-2,4,6,8-tetraenoic acid represented by the following Formula I

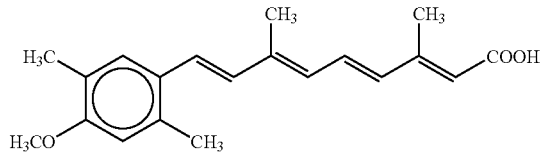

FORMULA I

The tetraene side chain in acitretin exists in all -trans configuration. The synthesis of acitretin involves a number of steps to build the tetraene side chain and generally results in a complex mixture of unwanted cis-trans isomers along with the desired all-trans product. Hitherto known processes for the preparation of acitretin either give impure product or involve a large number of steps. Thus, they are commercially not viable as they give low yield and involve cumbersome purification steps.

Acitretin was disclosed for the first time in U.S. Pat. No. 4,105,681 which, inter alia, describes several synthetic methods for the preparation of acitretin. All of these employ Wittig reaction or its modifications such as Wittig-Horner procedure and give a mixture of stereoisomers. Our attempts at preparing acitretin of the desired purity by following the processes taught in Examples 1 to 3 of the '681 patent were unsuccessful. A similar Witting process has been illustrated in DE 2636879 (Example 6) to give only 47% of the all trans-isomer along with 51% of the 11-cis isomer, as an impurity.

Alternative synthetic routes have been reported in Spanish patent, ES 2028649 and Helv. Chim. Acta. 370 (1989) which also give a mixture of cis-trans isomers.

The synthesis of all trans-isomer exclusively has been attempted in recent years. One such process has been described in Zh. Org. Chim. 792 (1989) which involves large number of steps thereby giving very low overall yield. The synthetic procedures cited in Biorg. Khim. 541 (1988), Khim. Farm. Zh. 43(1994) and Russian Patent No. 2001903 involve column chromatography at the intermediate or penultimate stages of preparation of acitretin which renders them unattractive for operation on industrial scale.

In light of the above drawbacks in the prior art processes, there is a need for the development of a simple and efficient process for the preparation of desired all trans-isomer of 9-(4-methoxy-2,3,6-trimethylphenyl)-3,7-dimethylnona-2,4,6,8-tetraenoic acid (acitretin) in high purity.

SUMMARY OF THE INVENTION

The present invention overcomes the problems associated with prior art and provides a practical process for the isolation of substantially pure acitretin from a complex mixture of cis-trans isomers involving solvent treatment. The invention avoids the tedious and cumbersome purification process of column chromatography and has obvious benefits with respect to economics and convenience to operate on a commercial scale.

In particular, the present invention relates to a process for the preparation of substantially pure acitretin of formula I

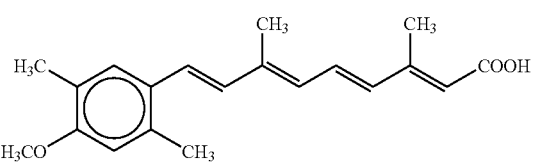

FORMULA I comprising:
contacting crude acitretin with solvent(s), optionally in the presence of a free radical scavenger, and
isolating substantially pure acitretin from a mixture thereof.

In the meaning of the present invention, the term "contacting" includes stirring, slurrying, dissolving, or a combination thereof.

The isolation may be accomplished by, for example, concentration, cooling, addition of a second solvent, filtration, or a combination thereof.

The solvent may be a ketone, an alcohol, a cyclic ether, a nitrile, water, or a mixture thereof. Examples of ketones include acetone, methylisobutyl ketone, and the like. Alcohols include methanol, ethanol, isopropanol, and the like. Examples of cyclic ethers include tetrahydrofuran, dioxane, and the like. Examples of nitriles include acetonitrile, and the like.

A free radical scavenger may be added along with a solvent to avoid decomposition/isomerization of acitretin. Examples of free radical scavengers that may be used in the present invention include butylated hydroxyanisole (BHA), butylated hydroxytoluene (BHT), and the like.

In the meaning of the present invention, "crude acitretin" is acitretin containing a mixture of various cis-trans isomers as impurities. Crude acitretin may be obtained by any of the synthetic routes described in the prior art.

In the meaning of the present invention, "substantially pure acitretin" includes acitretin having an assay of 98% or more by HPLC.

The second solvent which may be added during the isolation process may be an ester, a ketone, a chlorinated hydrocarbon, a cyclic ether, a nitrile, an alcohol, water, or a mixture thereof.

Examples of ketones include acetone, methylisobutyl ketone, and the like. Alcohols include methanol, ethanol, isopropanol, and the like. Examples of cyclic ethers include tetrahydrofuran, dioxane, and the like. Examples of nitriles include acetonitrile, and the like.

Examples of esters that may be used include ethyl acetate, butyl acetate, and the like. Examples of chlorinated hydrocarbons include dichloromethane, dichloroethane, and the like.

The scope of the present invention includes a process wherein the steps of contacting and isolation may be repeated to achieve the desired results.

DETAILED DESCRIPTION OF THE INVENTION

In the following section preferred embodiments are described by way of examples to illustrate the process of the invention. However, these are not intended in any way to limit the scope of the present invention.

EXAMPLE 1

Crude acetretin (10 g) was added to acetone (300 ml) and stirred at 25–30° C. for 1 hour under nitrogen atmosphere. The suspension was then filtered, washed with acetone (100 ml) and dried under vacuum at 25–30° C. to obtain pure acitretin (8 g, Assay 98.3% by HPLC).

EXAMPLE 2

Crude acetretin (10 g) and butylated hydroxyanisole (0.5 g) were dissolved in tetrahydrofuran (350 ml) at room temperature. The resultant solution was filtered and washed with tetrahydrofuran. The combined filtrate was concentrated under vacuum at 30–35° C. Acetone (100 ml) was added to the residue and stirred for 10 minutes at room temperature. The crystalline product so obtained was filtered, washed with acetone and dried at 25–30° C. under vacuum to obtain pure acitretin (8.2 g, assay 99.4% by HPLC).

While the present invention has been described in terms of its specific embodiments, certain modifications and equivalents will be apparent to those skilled in the art and are intended to be included within the scope of the present invention.

We claim:

1. A process for the preparation of substantially pure acitretin of Formula I,

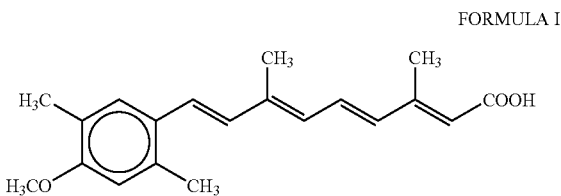

FORMULA I the process comprising:
contacting crude acitretin with solvent(s), in the presence of a free radical scavenger, wherein the free radical scavenger is butylated hydroxy anisole or butylated hydroxy toluene, and
isolating the substantially pure acitretin, from a mixture thereof.

2. The process of claim 1 wherein the solvent is a ketone, an alcohol, a cyclic ether, a nitrile, water, or a mixture thereof.

3. The process of claim 2 wherein the solvent is selected from the group consisting of acetone, methanol, tetrahydrofuran, acetonitrile, water, and a mixture thereof.

4. The process of claim 1 which comprises isolating substantially pure acitretin by removal of the solvent and/or by further adding a second solvent.

5. The process of claim 4 wherein the second solvent is an alcohol, a ketone, a chlorinated hydrocarbon, a cyclic ether, a nitrile, an ester, water, or a mixture thereof.

6. The process of claim 5 wherein the second solvent is selected from the group consisting of methanol, ethanol, isopropanol, acetone, methylisobutyl ketone, dichloromethane, dichloroethane, tetrahydrofuran, dioxane, acetonitrile, ethyl acetate, and a mixture thereof.

* * * * *